United States Patent
Ufkes et al.

(10) Patent No.: US 10,585,218 B2
(45) Date of Patent: Mar. 10, 2020

(54) APPARATUS AND METHOD FOR REDUCING DOSAGE TIME IN UV-C GERMICIDAL IRRADIATION

(71) Applicant: UD Innovations, LLC, Sullivan's Island, SC (US)

(72) Inventors: Philip J. Ufkes, Sullivan's Island, SC (US); Jeffery L. Deal, Charleston, SC (US)

(73) Assignee: UD Innovations, LLC, Sullivan's Island, SC (US)

( * ) Notice: Subject to any disclaimer, the term of this patent is extended or adjusted under 35 U.S.C. 154(b) by 0 days.

(21) Appl. No.: 15/887,218

(22) Filed: Feb. 2, 2018

(65) Prior Publication Data

US 2018/0224584 A1    Aug. 9, 2018

Related U.S. Application Data

(60) Provisional application No. 62/454,097, filed on Feb. 3, 2017.

(51) Int. Cl.
| | | |
|---|---|---|
| *G02B 5/08* | (2006.01) | |
| *A61L 2/10* | (2006.01) | |

(Continued)

(52) U.S. Cl.
CPC ............. *G02B 5/0891* (2013.01); *A61L 2/10* (2013.01); *A61L 2/26* (2013.01); *A61L 9/20* (2013.01);

(Continued)

(58) Field of Classification Search
CPC ..... A61L 2/08; A61L 2/10; A61L 2/24; A61L 2/26; A61L 2202/11; A61L 2202/14; A61L 2202/25; G02B 5/0891
See application file for complete search history.

(56) References Cited

U.S. PATENT DOCUMENTS

| 5,628,303 A | 5/1997 | Ahmady et al. |
| 6,078,425 A | 6/2000 | Wolfe et al. |

(Continued)

FOREIGN PATENT DOCUMENTS

| DE | 202014001022 U1 * | 5/2015 | ............ B32B 27/08 |
| WO | 2016069701 A1 | 5/2016 | |

OTHER PUBLICATIONS

International search report, International application No. PCT/US2018/013528, dated Mar. 28, 2018. ISA/US, Alexandria, VA.

(Continued)

*Primary Examiner* — David E Smith
(74) *Attorney, Agent, or Firm* — Gregory Finch; Finch Paolino, LLC

(57) ABSTRACT

An apparatus and method for reducing dosage time in ultraviolet germicidal irradiation systems. UV-C reflective adhesive film may be configured as sheets, or in a roll that may be cut to a desired size or shape. A user may apply UV-C reflective adhesive film to a desired surface of an interior room by exposing an adhesive surface to the desired interior surface. A reflective layer of the UV-C reflective adhesive film is configured to improve the reflectance percentage or reflectance pattern of a desired interior surface with respect to incident UV-C or near UV-C light. The improved reflectance properties of the desired surface functions to reflect a greater amount of light back to one or more closed-loop sensors in operation with a UV-C or near UV-C germicidal irradiation system. The improved reflectance thereby reduces the amount of time required for one or more closed-loop sensors in operation with a UV-C or near UV-C germicidal irradiation system to measure an effective kill-dose for surface disinfection.

19 Claims, 3 Drawing Sheets

(51) Int. Cl.
*A61L 2/26* (2006.01)
*A61L 9/20* (2006.01)

(52) U.S. Cl.
CPC ........ *A61L 2202/11* (2013.01); *A61L 2202/14* (2013.01); *A61L 2202/25* (2013.01)

(56) References Cited

U.S. PATENT DOCUMENTS

| | | | |
|---|---|---|---|
| 6,656,424 | B1 | 12/2003 | Deal |
| 6,911,177 | B2 | 6/2005 | Deal |
| 7,175,806 | B2 | 2/2007 | Deal et al. |
| 7,459,694 | B2 | 12/2008 | Scheir et al. |
| 7,754,156 | B2 | 7/2010 | Hyde et al. |
| 7,763,212 | B2 | 7/2010 | McEllen |
| 7,829,016 | B2 | 11/2010 | Deal et al. |
| 8,067,750 | B2 | 11/2011 | Deal |
| 8,114,342 | B2 | 2/2012 | Jung et al. |
| 8,178,042 | B2 | 5/2012 | Jung et al. |
| 8,226,887 | B2 | 7/2012 | Harmon et al. |
| 8,398,264 | B2 | 3/2013 | Anderson et al. |
| 8,455,832 | B2 | 6/2013 | Statham et al. |
| 8,575,567 | B2 | 11/2013 | Lyslo et al. |
| 8,584,612 | B2 | 11/2013 | Hart et al. |
| 8,859,994 | B2 | 10/2014 | Deal |
| 8,932,535 | B2 | 1/2015 | Hyde et al. |
| 9,039,966 | B2 | 5/2015 | Anderson et al. |
| 9,205,162 | B2 | 12/2015 | Deal et al. |
| 9,358,313 | B2 * | 6/2016 | Deal ........................ A61L 2/10 |
| 9,370,600 | B1 | 6/2016 | DuPuis et al. |
| 9,657,177 | B1 | 5/2017 | Pringle et al. |
| 2002/0192361 | A1* | 12/2002 | Chang .................... G01J 1/429 427/58 |
| 2006/0215257 | A1* | 9/2006 | Morrow ................. A61L 9/205 359/355 |
| 2007/0023710 | A1 | 2/2007 | Tom et al. |
| 2008/0019861 | A1* | 1/2008 | Silderhuis ................ A61L 9/16 422/3 |
| 2010/0060194 | A1 | 3/2010 | Furry et al. |
| 2012/0121457 | A1 | 5/2012 | Farren |
| 2012/0287677 | A1* | 11/2012 | Wheatley ............. G02B 6/0051 362/627 |
| 2012/0308784 | A1 | 12/2012 | Chen |
| 2013/0330235 | A1 | 12/2013 | Stibich et al. |
| 2014/0044590 | A1 | 2/2014 | Trapani |
| 2014/0131595 | A1 | 5/2014 | Nathan et al. |
| 2015/0062893 | A1 | 3/2015 | Lynn et al. |
| 2015/0086420 | A1 | 3/2015 | Trapani |
| 2015/0217012 | A1 | 8/2015 | Garner et al. |
| 2015/0250914 | A1* | 9/2015 | Aeifin ..................... A61L 9/205 422/4 |
| 2016/0046839 | A1* | 2/2016 | Maruno .................... C09J 7/50 428/336 |
| 2016/0058020 | A1 | 3/2016 | Shur et al. |
| 2016/0067365 | A1 | 3/2016 | Ma et al. |
| 2016/0122082 | A1* | 5/2016 | Butz ........................ B32B 1/02 215/12.1 |
| 2016/0219859 | A1 | 8/2016 | Deal |
| 2016/0271281 | A1 | 9/2016 | Clynne et al. |
| 2016/0271803 | A1 | 9/2016 | Stewart |
| 2016/0296649 | A1 | 10/2016 | Ramanand et al. |
| 2016/0375166 | A1 | 12/2016 | Kreitenberg |

OTHER PUBLICATIONS

International search report, International application No. PCT/US2018/013516, dated Apr. 4, 2018. ISA/US, Alexandria, VA.
Indigo-Clean. 3 pages. Accessed online Jan. 11, 2018 at https://Kenall.com/Indigo-Clean.Kenall, Kenosha, WI.
International search report, International application No. PCT/US2018/016666, dated Jun. 8, 2018. ISA/US, Alexandria, VA.
Rutala, W. et al., "Rapid Hospital Room Decontamination Using Ultraviolet (UV) Light with a Nanostructured UV-Reflective Wall Coating." Infection Control and Hospital Epidemiology. vol. 34, No. 5, pp. 527-529. May 2013. Cambridge University Press, Cambridge, UK.

* cited by examiner

APPARATUS AND METHOD FOR REDUCING DOSAGE TIME IN UV-C GERMICIDAL IRRADIATION

CROSS-REFERENCE TO RELATED APPLICATIONS

This application claims the benefit of U.S. Provisional Application Ser. No. 62/454,097, filed on Feb. 3, 2017 entitled "APPARATUS AND METHOD FOR REDUCING DOSAGE TIME IN UV-C GERMICIDAL IRRADIATION", the disclosure of which is hereby incorporated in its entirety at least by reference.

BACKGROUND OF THE INVENTION

1. Field of the Invention

The present invention relates to methods and devices for bacterial, fungal and/or viral sterilization and disinfection; and, is more particularly directed to an apparatus and method for reducing dosage time in ultraviolet germicidal irradiation.

2. Description of Related Art

Ultraviolet germicidal irradiation (UVGI) is a disinfection method that uses short-wavelength ultraviolet (UV-C) light to kill or inactivate microorganisms. One mechanism by which UV-C deactivates microorganisms is by destroying nucleic acids and disrupting their DNA, leaving them unable to perform vital cellular functions. The administration of UV-C radiation is becoming widely adopted by many hospitals as a more effective and reliable means of surface disinfection, as compared to the use of chemical cleaning agents alone. The effectiveness of germicidal UV-C irradiation depends on factors such as the length of time a microorganism is exposed to UV-C, the intensity and wavelength of the UV-C radiation, the presence of particles that can protect the microorganisms from UV, and a microorganism's ability to withstand UV-C during its exposure. In air and surface disinfection applications, the UV effectiveness is estimated by calculating the UV dose to be delivered to the microbial population. A method of calculating UV dose is as follows: UV dose $\mu Ws/cm^2$=UV intensity $\mu W/cm^2 \times$Exposure time (seconds).

Germicidal UV for disinfection is most typically generated by a mercury-vapor lamp. Low-pressure mercury vapor has a strong emission line at 254 nm, which is within the range of wavelengths that demonstrate strong disinfection effect. The optimal wavelengths for disinfection are close to 265 nm. UV-C LEDs use semiconductors to emit light between 255 nm-280 nm. The wavelength emission is tunable by adjusting the material of the semiconductor. Although the germicidal properties of ultraviolet (UV) light have long been known, it is only comparatively recently that the antimicrobial properties of visible violet-blue 405 nm light have been discovered and used for environmental disinfection and infection control applications. A large body of scientific evidence is now available that provides underpinning knowledge of the 405 nm light-induced photodynamic inactivation process involved in the destruction of a wide range of prokaryotic and eukaryotic microbial species, including resistant forms such as bacterial and fungal spores. Violet-blue light, particularly 405 nm light, has significant antimicrobial properties against a wide range of bacterial and fungal pathogens and, although germicidal efficacy is lower than UV light, this limitation is offset by its facility for safe, continuous use in occupied environments.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An object of the present disclosure is a UV-C reflective adhesive film comprising a UV-C reflective layer, the UV-C reflective layer comprising one or more metallic elements, the one or more metallic elements having a reflectance percentage in the range of about 50% to about 90% for light wavelengths in the range of about 200 nanometers to about 500 nanometers; a substrate layer, the UV-C reflective layer being disposed upon a first surface of the substrate layer; and, an adhesive layer being disposed upon a second surface of the substrate layer.

Another object of the present disclosure is a method for reducing dosage time in UV-C germicidal irradiation applications, the method comprising applying a UV-C reflective adhesive film to a target surface of an interior room, the UV-C reflective adhesive film having one or more metallic elements having a reflectance percentage in the range of about 50% to about 90% for light wavelengths in the range of about 200 nanometers to about 500 nanometers; emitting, with one or more LED emitters, a desired intensity of short wavelength light in the range of about 265 nanometers to about 405 nanometers to the target surface of the interior room; receiving, with one or more short wavelength light sensors, reflected light from the target surface of the interior room; and, measuring, with one or more processors operably engaged with the one or more short wavelength light sensors, an effective dose of short wavelength light from the one or more LED emitters for germicidal irradiation.

Yet another object of the present disclosure is a UV-C reflective adhesive film comprising a UV-C a UV-C reflective surface, the UV-C reflective surface comprising one or more metallic elements, the one or more metallic elements having a reflectance percentage in the range of about 50% to about 90% for light wavelengths in the range of about 200 nanometers to about 500 nanometers; and, an adhesive surface operable to couple the UV-C reflective adhesive film to a desired interior surface.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which.

DETAILED DESCRIPTION

Figure 1:
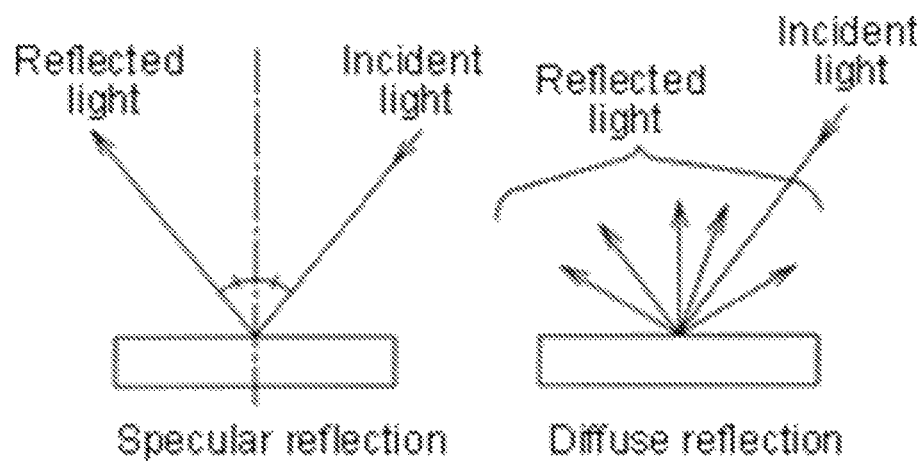
FIG. 1 is a concept diagram illustrating the difference between specular and diffuse reflection on a reflecting surface.

Exemplary embodiments are described herein to provide a detailed description of the present disclosure. Variations of these embodiments will be apparent to those of skill in the art. Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Embodiments of the present disclosure provide for an apparatus and method for reducing dosage time in ultraviolet germicidal irradiation systems. Various systems for germicidal irradiation are known in the prior art. Many of these systems function to employ one or more UV-C or near UV-C emitters for surface disinfection through emission of short wave radiation. These systems may utilize one or more closed-loop sensors operable to measure the amount of UV light or near UV light reflected from a target surface back to UV-C sensor during an irradiation cycle. The reflected light collected by the closed-loop sensors is measured by the system to determine the whether an effective dose for germicidal disinfection, or "kill dose," has been administered by the UV-C or near UV-C emitters to the target area. Germicidal irradiation systems generally operate on a "cycle," in which the UV-C emitters continue to deliver radiation to the room until the sensors have collected a predetermined kill dose of radiation. The time needed to deliver an effective kill dose, however, is not uniform across all surfaces—at least not from the perspective of the closed-loop sensor. This is due to varying reflectance properties across different surfaces and locations in an interior room. By way of example, a sensor will receive a higher rate of reflected UV-C radiation from a flat surface of a wall than it will in a corner. This is due to various factors such as angle of incidence and angle of reflected light, as well as reflectance percentage of the surface.

To illustrate the above concept, and in reference to FIG. 1, UV-C and near UV-C light is reflected from a surface according to the reflectance properties of that surface. A highly reflective and smooth surface, such as a mirror, may display specular (or near-specular) reflection and have a higher reflectance percentage, i.e. percentage of reflected vs. absorbed light. By contrast, a surface such as an interior wall that is not perfectly smooth and painted with matte paint, will have a lower reflectance percentage and will display a more diffuse reflection pattern. Likewise, the angle of the incident light affects the angle of the reflected light. This is the case for both diffuse and specular reflection. In the case of germicidal irradiation systems, interior surfaces with lower reflectance and/or more diffuse reflection properties will reflect less light back to the closed-loop sensors. As a result, it takes more time for the closed loop sensor to measure an effective kill-dose for the system; resulting in a longer disinfection cycle time and over-radiation of interior surfaces.

Figure 2:
FIG. 2 is a conceptual cross-section view of a UV-C reflective adhesive film, according to an embodiment.

Embodiments of the present disclosure provide for an apparatus and method for reducing dosage time in ultraviolet germicidal irradiation systems. Referring now to FIG. 2, a conceptual cross-section view of a UV-C reflective adhesive film 102 is shown. UV-C reflective adhesive film 102 may be configured as a sheet, or in a roll that may be cut to a desired size or shape. A user may apply UV-C reflective adhesive film 102 to a desired surface of an interior room by exposing an adhesive surface to the desired interior surface. A reflective layer of the UV-C reflective adhesive film 102 is configured to improve the reflectance percentage or reflectance pattern of a desired interior surface with respect to incident UV-C or near UV-C light. The improved reflectance properties of the desired surface as a result of UV-C reflective adhesive film 102 function to reflect a greater amount of light back to one or more closed-loop sensors in operation with a UV-C or near UV-C germicidal irradiation system. The improved reflectance of the target surface reduces the amount of time required for one or more closed-loop sensors, in operation with a UV-C or near UV-C germicidal irradiation system, to collect an effective kill-dose of radiation needed for surface disinfection.

According to an embodiment, a UV-C reflective adhesive film 102 is generally comprised of a reflective layer 202, a substrate layer 204 (optional), and an adhesive layer 206. Reflective layer 202 may be comprised of one or more metallic elements (or other reflective material) having a reflectance percentage in the range of about 50% to about 90% for wavelengths in the range of about 200 nanometers to about 500 nanometers. Reflective layer 202 may also have surface properties such that reflective layer 202 may be operable to reflect light according to a predetermined reflection angle or diffusion pattern. For example, surface properties may include varying texture or distribution of reflective or metallic material. Reflective layer 202 may be substantially smooth or may have a textured finish. Reflective layer 202 may be substantially homogeneous in distribution of reflective or textural properties, or may display varying or heterogeneous surface properties.

According to an embodiment, UV-C reflective adhesive film 102 may include a substrate layer 204. Substrate layer 204 may be any form of porous or non-porous surface substrate operable to form a surface layer for reflective layer 202 or a bonding surface for adhesive layer 206. In certain embodiments, UV-C reflective adhesive film 102 may be comprised of reflective layer 202 and adhesive layer 206. Adhesive layer 206 is bonded to reflective layer 202 or substrate layer 204. Adhesive layer 206 may have a protective, removable backing to protect the adhesive from exposure to air. Protective backings for adhesives are well known in the art and need not be discussed at length here. Adhesive layer 206 may be comprised of a reusable adhesive or a bonding adhesive. Alternatively, UV-C reflective adhesive film 102 may be comprised of only reflective layer 202 having a first reflective surface and a second adhesive surface, such that the second adhesive surface selectively couples UV-C reflective adhesive film 102 to a desired interior surface. Adhesive layer 206 may not include an adhesive, but may rather display adhesive properties sufficient to selectively couple to an interior surface.

Figure 3:
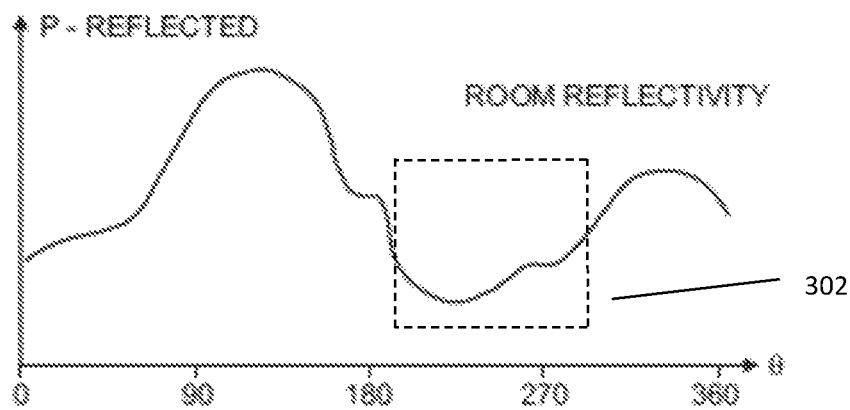
FIG. 3 is a plot of surface reflectance percentage at points along a 360 degree circumference in an interior room.

Referring now to FIG. 3, a plot of surface reflectance percentage at points along a 360 degree circumference of an interior room is shown. In the example illustrated in FIG. 3, the reflectance percentage of an interior room is measured along a 360 degree circumference from an approximate midpoint of the room. In this example, the surfaces of the interior room display strong reflectivity (e.g. approximately 80 percent) at location 100 degrees, and weak reflectivity (e.g. approximately 10 to 20 percent) at locations between 190 degrees to 260 degrees, i.e. interior room location 302. Interior room location may be a corner of the room, or may be a portion of the room with a matte or textured surface with poor reflectance. According to an embodiment, as further disclosed in FIG. 4 below, a user may apply a UV-C reflective adhesive film 102 to the wall surface of interior room location 302 in order to improve the reflectance of interior room location 302.

Figure 4:
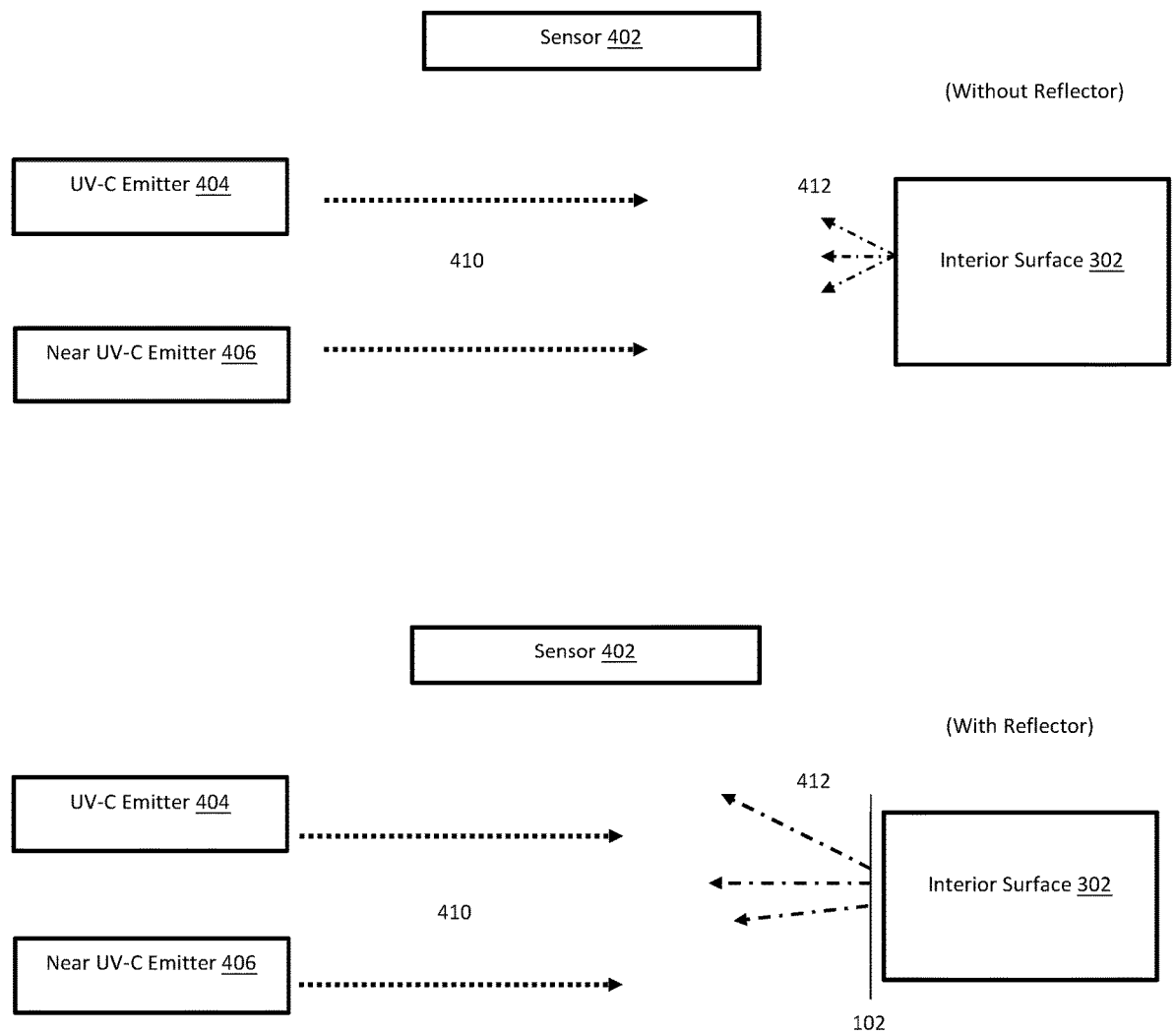
FIG. 4 is a block diagram illustrating the difference in short wave radiation reflectance of an interior surface, with and without a UV-C reflective adhesive film; and, FIG. 5 is a process flow diagram of a method for reducing UV-C germicidal irradiation dosage time, according to an embodiment.

Referring now to FIG. 4, a block diagram illustrating reflectance of an interior room location 302 is shown, with and without UV-C reflective adhesive film 102. According to an embodiment, UV-C emitter 404 and near UV-C emitter 406 emit short wave radiation 410 on interior surface 302. UV-C emitter 404 emits short wave radiation at wavelength of about 265 nanometers, and near UV-C emitter 406 may emit short wave radiation at wavelength of about 405 nanometers. Incident short wave radiation 410 is reflected from interior surface 302 as reflected light 412. Reflected light 412 is collected by sensor 402. Sensor 402 measures the amount of reflected light 412 to calculate a kill dose. Once sensor 402 receives a kill dose, a communication is made to UV-C emitter 404 and near UV-C emitter 406 to disengage emission 410. As illustrated in FIG. 4, interior surface 302 displays weak reflectivity (e.g. approximately 10 to 20 percent), and may display a diffusion pattern that is not optimal for reflecting light in the direction of sensor 402. In order to improve reflectivity and/or diffusion pattern, UV-C reflective adhesive film 102 is applied to interior surface 302. UV-C reflective adhesive film 102 has an adhesive surface and a reflecting surface, as described in FIG. 2, above. The adhesive surface is operable to selectively couple UV-C reflective adhesive film 102 to interior surface 302. The reflecting surface is operable to increase the reflectivity and/or steer the diffusion pattern of reflected light 412. The application of UV-C reflective adhesive film 102 on interior surface 302 results in improved reflectivity and/or optimized diffusion pattern(s) for reflected light 412 in relation to sensor 402. This results in more efficient collection of reflected light 412 by sensor 402, and in turn, shorter overall time needed for sensor 402 to collect a kill-dose of short wave radiation from interior surface 302.

Figure 5:
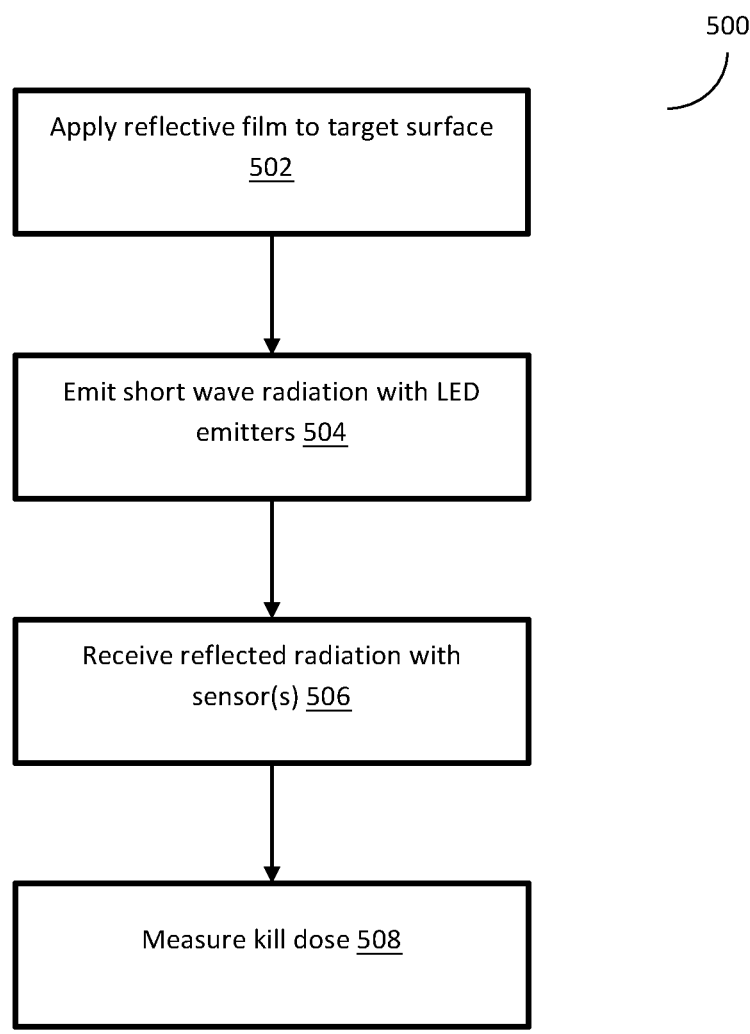

Referring now to FIG. 5, a process flow diagram of a method 500 for reducing UV-C germicidal irradiation dosage time is shown. According to an embodiment, a UV-C reflective adhesive film is applied to a target surface in an interior room 502. A target surface may be a corner of a room, as an example. A UV-C reflective adhesive film may have a reflective surface and an adhesive surface. The reflective surface may be comprised of one or more metallic elements (or other reflective material) having a reflectance percentage in the range of about 50% to about 90% for light wavelengths in the range of about 200 nanometers to about 500 nanometers. The reflective surface may also have surface properties such that the reflective layer may be operable to reflect light according to a predetermined reflection angle or diffusion pattern. The adhesive surface may contain an adhesive, or otherwise display adhesive properties, to selectively couple UV-C reflective adhesive film to a target surface in an interior room. The adhesive surface may be configured to be removed and reapplied to different surfaces in a target room. UV-C reflective adhesive film may be configured as a sheet or in a roll.

Continuing with the method 500 for reducing UV-C germicidal irradiation dosage time, LED emitters emit short wave radiation in the range of about 265 nanometers to about 405 nanometers to the target surface 504. Light reflected from the target surface is collected by one or more closed-loop sensors 506. A kill-dose is measured by the one or more closed-loop sensors in response to the collected light, and the germicidal irradiation is discontinued upon reaching a predetermined kill dose 508.

The present disclosure includes that contained in the appended claims as well as that of the foregoing description. Although this invention has been described in its exemplary forms with a certain degree of particularity, it is understood that the present disclosure has been made only by way of example and numerous changes in the details of construction and combination and arrangement of parts may be employed without departing from the spirit and scope of the invention.

What is claimed is:

1. A UV-C reflective adhesive film comprising:
    a UV-C reflective layer, the UV-C reflective layer comprising one or more metallic elements, the one or more metallic elements having a reflectance percentage in a range of 50% to 90% for light wavelengths in a range of about 200 nanometers to about 500 nanometers;
    a substrate layer, the UV-C reflective layer being disposed upon a first surface of the substrate layer; and
    an adhesive layer, the adhesive layer being disposed upon a second surface of the substrate layer such that the UV-C reflective adhesive film is selectively coupled to an interior side of a target surface,
        wherein the UV-C reflective layer comprises one or more surface properties operable to reflect light according to a predetermined diffusion pattern, the UV-C reflective layer being configured to steer the diffusion pattern of reflected light towards a sensor.

2. The UV-C reflective adhesive film of claim 1, wherein the UV-C reflective layer comprises one or more surface properties having a substantially homogeneous distribution.

3. The UV-C reflective adhesive film of claim 1, wherein the UV-C reflective layer comprises one or more surface properties having a substantially heterogeneous distribution.

4. The UV-C reflective adhesive film of claim 1, wherein the UV-C reflective layer is substantially smooth.

5. The UV-C reflective adhesive film of claim 1, wherein the UV-C reflective layer is substantially textured.

6. The UV-C reflective adhesive film of claim 1, wherein the substrate layer is constructed from a porous substrate.

7. The UV-C reflective adhesive film of claim 1, wherein the substrate layer is constructed from a non-porous substrate.

8. A method for reducing dosage time in UV-C germicidal irradiation applications, the method comprising:
    applying the UV-C reflective adhesive film of claim 1 to the interior side of the target surface, the UV-C reflective adhesive film having one or more metallic elements having a reflectance percentage in a range of 50% to 90% for light wavelengths in a range of about 200 nanometers to about 500 nanometers, wherein the UV-C reflective adhesive film comprises one or more surface properties operable to reflect light according to a predetermined diffusion pattern;

emitting, with one or more LED emitters, a desired intensity of short wavelength light in a range of about 265 nanometers to about 405 nanometers to the target surface of the interior room;

receiving, with one or more short wavelength light sensors, reflected light from the target surface; and, measuring, with one or more processors operably engaged with the one or more short wavelength light sensors, an effective dose of short wavelength light from the one or more LED emitters for germicidal irradiation.

9. The method for reducing dosage time in UV-C germicidal irradiation applications of claim 8, further comprising discontinuing the emission of the desired intensity of short wavelength light once the effective dose is measured.

10. The method for reducing dosage time in UV-C germicidal irradiation applications of claim 8, wherein the UV-C reflective adhesive film is operable to steer the reflective light towards the one or more short wavelength light sensors.

11. The method for reducing dosage time in UV-C germicidal irradiation applications of claim 8, wherein the one or more short wavelength light sensors are closed-loop sensors.

12. The UV-C adhesive film according to claim 1, wherein the UV-C adhesive film consists of the UV-C reflective layer, the substrate layer, and the adhesive layer.

13. The UV-C adhesive film according to claim 12, wherein the UV-C reflective layer further comprises one or more surface properties operable to reflect light according to a predetermined reflection angle.

14. A UV-C reflective adhesive film comprising:

a UV-C reflective surface, the UV-C reflective surface comprising one or more metallic elements, the one or more metallic elements having a reflectance percentage in a range of 50% to 90% for light wavelengths in a range of about 200 nanometers to about 500 nanometers, wherein the UV-reflective surface is substantially textured, comprises one or more surface properties having a substantially heterogeneous distribution, and is configured to steer a diffusion pattern of reflected light towards a sensor; and an adhesive surface operable to couple the UV-C reflective adhesive film to an interior side of a target surface.

15. The UV-C reflective adhesive film of claim 14, wherein the adhesive surface is comprised of a reusable adhesive.

16. The UV-C reflective adhesive film of claim 14, wherein the adhesive surface is comprised of a bonding adhesive.

17. A UV-C reflective adhesive film comprising:

a UV-C reflective layer, the UV-C reflective layer comprising one or more metallic elements, the one or more metallic elements having a reflectance percentage in a range of 50% to 90% for light wavelengths in a range of about 200 nanometers to about 500 nanometers, wherein the UV-reflective layer is substantially smooth, comprises one or more surface properties having a substantially homogeneous distribution, and is configured to steer a diffusion pattern of reflected light towards a sensor; and a substrate layer, the UV-C reflective layer being disposed upon a first surface of the substrate layer; and an adhesive layer, the adhesive layer being disposed upon a second surface of the substrate layer such that the UV-C reflective film is selectively coupled to an interior side of a target surface, wherein the UV-C reflective layer comprises one or more surface properties operable to reflect light according to a predetermined diffusion pattern.

18. The UV-reflective adhesive film of claim 17, wherein the UV-C reflective adhesive film consists of the UV-reflective layer, the substrate layer, and the adhesive layer.

19. The UV-C reflective adhesive film of claim 17, wherein the UV-C reflective layer further comprises one or more surface properties operable to reflect light according to a predetermined reflection angle.

* * * * *